United States Patent
Adamoli et al.

(10) Patent No.: US 7,442,411 B2
(45) Date of Patent: Oct. 28, 2008

(54) METHOD OF INSTALLING WETTED BUILDING INSULATION MATERIALS

(76) Inventors: James A. Adamoli, 14343 Lost Meadow La., Houston, TX (US) 77079; Mark A. Adamoli, 14343 Lost Meadow La., Houston, TX (US) 77079

( * ) Notice: Subject to any disclaimer, the term of this patent is extended or adjusted under 35 U.S.C. 154(b) by 315 days.

(21) Appl. No.: 11/179,259

(22) Filed: Jul. 12, 2005

(65) Prior Publication Data

US 2007/0014931 A1    Jan. 18, 2007

(51) Int. Cl.
*B05D 7/24* (2006.01)
(52) U.S. Cl. .................................. 427/243; 427/427.4
(58) Field of Classification Search ................ 427/243, 427/244, 427.4
See application file for complete search history.

(56) References Cited

U.S. PATENT DOCUMENTS

| | | | | |
|---|---|---|---|---|
| 4,463,039 A | * | 7/1984 | O'Connell et al. ....... | 427/427.4 |
| 5,641,368 A | * | 6/1997 | Romes et al. ................. | 156/71 |
| 2005/0066537 A1 | * | 3/2005 | Kahner et al. .................. | 34/90 |
| 2006/0165885 A1 | * | 7/2006 | Fay ............................ | 427/206 |

OTHER PUBLICATIONS www.moldacrossamerica.org website, Dec. 21, 2004 version, 3 pages.*

* cited by examiner

*Primary Examiner*—Frederick J Parker

(57) ABSTRACT

The invention is a method comprising the steps of wetting insulating materials with an aqueous solution containing an amount of a mold inhibitor such as chlorine, in an amount effective to inhibit microbial growth on the materials, and in one form, sterilize existing microbial growth in the cavity in which the insulating materials are to be placed; and placing the insulating materials into a portion of the structure. The method provides an advantageous and low cost process for the placement of wetted insulation materials that reduces the time required to complete closure of the insulated portion of the building while (1) minimizing the risk of undesirable growth of molds, fungi and the like and (2) sterilizing surfaces contacted by aqueous solution or wetted materials.

11 Claims, No Drawings

METHOD OF INSTALLING WETTED BUILDING INSULATION MATERIALS

FIELD OF THE INVENTION

This invention relates to an improved method for sterilizing existing microbe growth and inhibiting further microbe growth in building installations and, in particular, in building insulation and the areas in which the insulation is used. The invention further relates to chemical compositions that can be used in the method.

BACKGROUND OF THE INVENTION

Fiberglass, rockwool and cellulose-based materials are commonly used as building insulation. All have the benefit of having very good insulation performance (high so-called "R-values"). Fiberglass and rockwool are often installed in the form of batting which is stapled in wall cavities (such as between supporting members) in a structure. However, fiberglass, rockwool and cellulose based materials can be placed in such cavities by being blown into place as loose fill. When installed in this fashion, the material tends to conform to and more completely fill the cavity. That is, fiberglass batting does not conform as closely to framing, piping, wiring and other in-wall obstructions as does blown insulation. Thus, blown materials more completely fill the cavity and better limit air infiltration into and through the cavities in which they are placed.

It is known that blown cellulose insulation (typically made from recycled paper treated with fire-retardant chemicals such as boric acid and ammonia sulfate) can be even more effectively placed through a combination of pneumatic blowing and hydraulic spraying. In such methods, the insulation is pneumatically blown into a wall cavity through a two and one-half inch or larger diameter flexible hose connected to an insulation-blowing machine. The hose outlet is fitted with spray tips that are in-turn connected to a high-pressure water source (e.g. 150 p.s.i.). As the insulation is blown into a cavity it is mixed with the spray water. As water is absorbed into or becomes attached to the surface of the material it becomes heavier and stickier which allows the material to pack and more completely fill the wall cavity. Since the insulating material is more densely packed thoroughly filling the cavity, the insulation performance is improved over installations in which only dry material is blown into place.

There are drawbacks to using wetted insulation materials. In order to avoid possible microbial growth it is appropriate to dry the wetted insulation. Drying occurs much faster when the insulation in the cavity remains exposed, so all or some drying is done before proceeding with closure of the insulated cavity. The time necessary for this drying step depends on the amount of water used in the process, ambient humidity, the thickness of the material deposited in the wall, and fresh air flow after the process. Typically the insulation as deposited will range from 30-60% moisture. It is desirable to dry the material to no more than about 18% moisture before closing the wall.

Closing the wall before the insulation is adequately dried increases the risk of mold growth on the insulation, the framing members, gypsum board and the interior walls. This is particularly the case with insulation materials that include fire retardants that may actually promote mold growth (ammonia sulfate). However, the need to move quickly during a construction project makes it difficult to wait the 24-60 hours that can be required to permit the insulation to dry adequately before closing the wall or other cavity. This practical consideration has limited the use of wetted insulation materials, despite their long-term beneficial impacts on energy savings.

SUMMARY OF THE INVENTION

The present invention is a method of installing wetted insulation materials, which method eliminates the need for extended periods of drying by minimizing the risk of microbial growth in the insulated cavity while the insulation is wet. The method comprises the steps of preparing loose fill (sometimes referred to as "stabilized insulation" where a dry adhesive has been incorporated into the insulation material during its manufacture; sometimes referred to as "spray-on insulation" where a liquid adhesive is used to apply the insulation material) insulative materials, placing the materials into a cavity to be insulated, and wetting the materials with a dilute aqueous solution comprising a mold growth inhibitor such as chlorine in an amount effective to inhibit mold growth. In a preferred form of the invention, hypochlorite bleach is used as a chlorine source and the insulation is placed by blowing, e.g. pneumatically, and using a fine, high-pressure water spray. The insulative materials are selected from high R-value materials such as cellulose, rockwool and fiberglass.

DETAILED DESCRIPTION OF THE INVENTION

The present invention is directed to an improved method for sanitizing areas within a building (either completed or during construction) in which an area that is wetted is treated (preferably simultaneously) with a sanitizing agent or mold growth inhibitor such as chlorine. The source of the chlorine may be chlorine bleach, especially hypochlorite bleach.

The method is a particularly cost effective method for sanitizing wetted insulation and the areas in contact with these materials. While it is clear that insulation materials that are wet-deposited provide better insulation in the long run than dry-deposited materials, the fear that mold, mildew, fungi and other growths can occur results in either avoidance of the use of wet in favor of dry materials, or the need to permit the materials to dry once in place. In the latter case, extended drying times are necessary, though highly undesirable. The method of the present invention reduces the need for such extended drying times by permitting an insulated cavity to be sealed while the insulation is wetter than would be preferred otherwise. Using a wetting solution containing a mold inhibitor such as chlorine inhibits the growth of mold and other undesirable microbes. The term "mold" is used in the balance of this specification to mean a range of microbes (mold, fungi, mildew etc.), the growth of which are undesirable in buildings.

Various types of sanitizing or mold growth inhibiting agents may be used in the invention, so long as they may be incorporated into an aqueous solution in amounts suitable to achieve the necessary degree of microbial growth inhibition. Most advantageously it has been found that small amounts of hypochlorite bleach can be used to provide chlorine in the process. Hypochlorite bleach is well known as a bleaching agent for laundry use. It is generally formulated at a concentration of about 4-8% in water for household use, where it is typically diluted to a concentration of about 200 ppm sodium hypochlorite for laundry bleaching. It is relatively inexpensive, safe to handle and widely available.

This form of the invention provides a simple and inexpensive solution because the chlorine containing solution can be created at a job site by simply adding sodium hypochlorite bleach in an appropriate amount to a water tank that is already used for wet insulation applications.

Different insulating materials can be used in the method of the invention, which materials are well known in the art, such as cellulose (i.e. ground waste paper combined with fire retardant chemicals) and fiberglass. Typically, these insulation materials are procured in the form of dry pieces. In this invention, the materials will be placed in an open cavity or portion of a structure, such as a building under construction or a completed building (a wall, sub-floor or attic). In order to enhance the ultimate performance of the materials, it is preferred that they be placed in a manner which will minimize the movement of air across the cavity or portion, so-called air infiltration. By wetting the materials as they are placed, the insulation will tend to pack more densely, fill the cavity more completely and conform closely to objects that may be found in the cavity such as pipes, electrical conduits and wiring and the like.

In order to attain such close packing, the materials should be wetted to at least about 20% by weight with the wetting solution being used, though wetting of greater than 30% or 40% by weight is often useful. The degree of wetting referred to herein is as measured in bulk. For example, a mixture could comprise 50 pounds of dry cellulose insulation material onto which is incorporated 46 pounds of water so that the insulation forms 52% of the mixture and the water is 48%.

The amount of water incorporated may also depend on the type of installation. For example, in attic installations it is useful to minimize the amount and weight of the installed insulation to achieve a given level of insulation performance. In these types of installations, insulation treated with an adhesive can be used. In this case the water is applied in an amount effective to control dust and activate a dry adhesive (starch, clay, etc.) manufactured in the material (e.g. 10-15%) which prevents the cellulose insulation material from settling so much. In this type application, a spray nozzle or nozzles internal to the blowing hose can be used, located close to the insulation-blowing machine. The insulation material containing the dry adhesive passes through a fine water spray inside the hose, traveling through the hose where the adhesive is activated and begins to dry as it is placed in the attic.

In order to prepare the solution necessary for use in the invention, liquid chlorine bleach is measured into the feed tank or drum from which spray water will be drawn. In order to provide a homogenous solution, some level of mixing is desired, though agitation from movement of the tank at the job site will typically suffice. For the installation of wetted insulation, pieces of dry insulation made from waste paper are loaded to a hopper from which an insulation blowing flex tube is fed. Spray nozzles are mounted within or at the end of the insulation blowing tube so that the solution from the liquid feed tank is applied to the insulation as they pass through or out of the tube and are directed to the cavity in the building to be insulated. A hose or hoses leading from the tank to the spray nozzle(s) includes a valve mechanism for the nozzle and/or water pump that permits the flow rate of the solution to be set as desired, and therefore the amount of aqueous solution to be applied to be set as desired for a particular installation and insulation material. Likewise, the amount of insulation passing through the tube can be metered.

Once the wetted/treated insulation has been placed in the portion or cavity, that portion or cavity can be closed. In particular, unlike the prior methods for the placement of wet insulation, it is not required that the insulation be permitted to dry for a significant period of time before the closure. This permits the builder to close wall or other portion of the structure based on timing that is otherwise appropriate for the project. Thus, closure of the portion of cavity can occur while the wetted material still contains greater than 20% by weight of the aqueous solution.

Depending on the amount of wetting desired, the method of the invention will also work if the insulation is wetted in a tank or other container to make a slurry of wetted insulation, which slurry is then deposited into the desired cavity.

Likewise, the insulation may be deposited dry and then wetted in place, though it is preferred if this method is used that placement occur in stages, i.e. where some amount of insulation is placed then wetted, additional amounts of insulation are placed and wetted, and so on. This is to minimize the amount of insulation that is not exposed to the mold growth inhibiting solution.

The solution used the in the inventive process should comprise chlorine in an amount which, when applied to the insulation pieces, is effective to inhibit mold growth on the pieces. In other embodiments, the inhibitor will be present in an amount sufficient to sterilize or reduce existing mold growth on framing members, gypsum board, insulation materials and others surfaces contacted. In such embodiments, the solution will comprise no less than 20 ppm chlorine and preferably greater than 50 ppm available chlorine. Since exposure times are relatively long, relatively weak solutions can be used and nevertheless be effective. Weaker solutions are advantageous from a materials handling standpoint.

It has been found that effective solutions can be prepared by mixing 0.0625 gallons of hypochlorite bleach (Clorox® brand) with 45 gallons of water. In one set of experiments, this ratio was used and chlorine concentration in the solution was measured in the tank, and then also tested after the solution was sprayed through nozzles, over a period of four days, to determine the amount of available chlorine in the solution.

|  | Tank (ppm) | After Spraying (ppm) |
| --- | --- | --- |
| Day 1 | 100 | 15, 80, 60 |
| Day 2 | 80 | 35, 60 |
| Day 3 | 40 | 30 |
| Day 4 | 35 | 20 |

While the measured chlorine amount was reduced over time, chlorine remained available through the fourth day of this test.

Tests were performed to learn the level of mold growth at various places at a site to be insulated and on the insulation:

| 1. Old Application (behind the wall) | |
| --- | --- |
| A | 2 CFU |
| B | 8 CFU |
| C | 5 CFU |
| 2. Before applying bleach containing solution (insulation materials) | |
| A | 18 CFU |
| B | 13 CFU |
| C | 20 CFU |
| 3. Right after applying the bleach containing solution (insulation materials) | |
| A | 11 |
| B | 7 |
| C | 2 |
| 4. Open space samples TNTC | |
| A | 80 |
| B | 35 |

CFU = colony forming units
TNTC = too numerous to count

From these tests it is concluded that a chlorine containing solution can effectively decrease the amount of mold on wetted insulation.

While only a limited number of embodiments are detailed in the present specification, it is be understood that there will be many variations of these which will be apparent to those skilled in the art. It is intended that such additional modifications be encompassed in the appended claims.

What is claimed is:

1. A method of placing insulative material in a structure comprising the steps of:
   (a) projecting pieces of insulative material into a portion of a structure using blown air;
   (b) wetting the pieces of insulative material with an aqueous wetting solution in an amount such that, in bulk, the insulative material contains greater than 20% by weight of the solution, the solution comprising a mold growth inhibitor in an amount which, when applied to the pieces, is effective to reduce existing mold growth on the portion of structure the pieces are blown into and inhibit mold growth on said pieces, and
   (c) enclosing the pieces insulative material in said portion while said material contains greater than 20% by weight of said solution.

2. The method of claim 1 comprising the step of wetting said pieces to an extent and in a concentration effective to inhibit mold growth for a period of time greater than the time necessary for the wetted pieces to dry to less than 20% by weight of said solution in said portion.

3. The method of claim 1 wherein said wetting step comprises the step of spraying said aqueous solution onto said pieces as they are projected.

4. The method of claim 1 wherein said aqueous solution comprises hypochlorite bleach.

5. The method of claim 1 wherein said solution comprises greater than 50 ppm available chlorine.

6. The method of claim 1, wherein the step of enclosing the pieces insulative material in said portion occurs while said material is densely packed.

7. A method of densely packing insulation in a structure comprising the steps of
   (a) wetting insulating materials with an aqueous solution containing an amount of chlorine effective to inhibit mold growth on said materials in an amount such that said material, in bulk, contains greater than 20% by weight of said solution as it is placed;
   (b) concurrently projecting pieces of said insulating materials into a portion of the structure using blown air wherein said amount of chlorine is effective to reduce existing mold growth on said portion to provide a structure having densely packed insulation.

8. The method of claim 7 wherein said aqueous solution comprises hypochlorite bleach.

9. The method of claim 7 wherein said solution comprises greater than 50 ppm available chlorine.

10. The method of claim 7 further comprising the step of enclosing said insulating material in said portion after said placing step.

11. The method of claim 10 further comprising the step of enclosing said insulating material in said portion while said material contains greater than 20% by weight of said solution.

* * * * *